US008755880B2

(12) United States Patent
Higuchi et al.

(10) Patent No.: US 8,755,880 B2
(45) Date of Patent: Jun. 17, 2014

(54) INTRAOCULAR IONTOPHORETIC DEVICE AND ASSOCIATED METHODS

(75) Inventors: John W. Higuchi, Salt Lake City, UT (US); S. Kevin Li, Cincinnati, OH (US)

(73) Assignee: Aciont, Inc., Salt Lake City, UT (US)

( * ) Notice: Subject to any disclaimer, the term of this patent is extended or adjusted under 35 U.S.C. 154(b) by 365 days.

(21) Appl. No.: 11/414,137

(22) Filed: Apr. 27, 2006

(65) Prior Publication Data

US 2007/0106278 A1    May 10, 2007

Related U.S. Application Data

(60) Provisional application No. 60/729,980, filed on Oct. 24, 2005.

(51) Int. Cl.
*A61N 1/30* (2006.01)

(52) U.S. Cl.
USPC .............. 604/20; 604/294; 604/501; 604/521

(58) Field of Classification Search
USPC ............................. 604/20, 21, 294, 501, 521
See application file for complete search history.

(56) References Cited

U.S. PATENT DOCUMENTS

| | | | |
|---|---|---|---|
| 4,955,378 A | 9/1990 | Grasso | |
| 5,560,816 A | 10/1996 | Robinson | |
| 6,001,088 A | 12/1999 | Roberts et al. | |
| 6,154,671 A | 11/2000 | Parel et al. | |
| 6,312,393 B1 | 11/2001 | Abreu | |
| 6,319,240 B1 | 11/2001 | Beck | |
| 6,324,424 B1 | 11/2001 | Ledger et al. | |
| 6,424,862 B1 | 7/2002 | Brown, III | |
| 6,442,423 B1 | 8/2002 | Domb et al. | |
| 6,539,251 B2 | 3/2003 | Beck et al. | |
| 6,579,276 B2 | 6/2003 | Lloyd et al. | |
| 6,662,044 B2 * | 12/2003 | Crawford et al. ............... 604/20 |
| 6,697,668 B2 | 2/2004 | Parkinson et al. | |
| 6,728,573 B1 | 4/2004 | Beck et al. | |
| 6,733,485 B1 | 5/2004 | Whitehurst et al. | |

(Continued)

FOREIGN PATENT DOCUMENTS

| WO | WO03/030989 | 4/2003 |
|---|---|---|
| WO | WO 03/039622 | 5/2003 |
| WO | WO03/043689 | 5/2003 |

OTHER PUBLICATIONS

U.S. Appl. No. 11/799,754, filed May 1, 2007, Higuchi et al. Office action issued May 19, 2009.

(Continued)

*Primary Examiner* — Laura Bouchelle
(74) *Attorney, Agent, or Firm* — Thorpe North & Western LLP (57) ABSTRACT

The present invention includes methods and devices for delivering an active agent into the eye of a subject. One such device may include an anode assembly having an anode housing and an anode configured to electrically couple to a power source, the anode assembly being configured to contact and remain against a surface of the eye. The device may also include a cathode assembly having a cathode housing and a cathode configured to electrically couple to the power source, the cathode assembly being configured to contact and remain against the surface of the eye. Additionally, the device may include at least one active agent reservoir functionally associated with at least one of the anode assembly and the cathode assembly.

21 Claims, 4 Drawing Sheets

(56) References Cited

U.S. PATENT DOCUMENTS

| | | | |
|---|---|---|---|
| 6,801,804 B2 | 10/2004 | Miller et al. | |
| 7,151,960 B1 | 12/2006 | Newsome | |
| 7,164,943 B2 | 1/2007 | Roy | |
| 7,346,389 B1* | 3/2008 | Newsome | 604/20 |
| 2002/0016575 A1 | 2/2002 | Beck et al. | |
| 2002/0038101 A1 | 3/2002 | Avrahami et al. | |
| 2002/0107508 A1 | 8/2002 | Burnett | |
| 2003/0088204 A1* | 5/2003 | Joshi | 604/20 |
| 2003/0225360 A1 | 12/2003 | Eppstein et al. | |
| 2004/0267188 A1* | 12/2004 | Behar et al. | 604/20 |
| 2005/0004509 A1* | 1/2005 | Sun et al. | 604/20 |
| 2005/0181018 A1 | 8/2005 | Peyman | |
| 2005/0245856 A1 | 11/2005 | Roy | |
| 2006/0036209 A1 | 2/2006 | Subramony et al. | |
| 2006/0036210 A1 | 2/2006 | Zhang et al. | |

OTHER PUBLICATIONS

U.S. Appl. No. 11/414,134, filed Apr. 27, 2006 Higuchi et al. Office Action issued Apr. 10, 2009.

Higuchi, U.S. Appl. No. 11/414,134, office action issued Dec. 18, 2009.

Higuchi, U.S. Appl. No. 11/799,754, office action issued Dec. 7, 2009.

U.S. Appl. No. 11/414,134, filed Apr. 27, 2006; John W. Higuchi; notice of allowance dated Sep. 13, 2013.

* cited by examiner

INTRAOCULAR IONTOPHORETIC DEVICE AND ASSOCIATED METHODS

PRIORITY DATA

This application claims the benefit of U.S. Provisional Patent Application Ser. No. 60/729,980, filed on Oct. 24, 2005, which is incorporated herein by reference. This application also claims the benefit of U.S. patent application Ser. Nos. 11/238,144 and 11/238,104, both filed on Sep. 27, 2005, both of which are incorporated herein by reference.

FIELD OF THE INVENTION

The present invention relates to systems, methods, and devices for the delivery of an active agent following minimally invasive or noninvasive delivery thereof through a localized region of a subject's body tissue, particularly the eye. Accordingly, the present invention involves the fields of chemistry, pharmaceutical sciences, and medicine, particularly ophthalmology.

BACKGROUND OF THE INVENTION

Posterior and intermediate eye diseases that require ocular drug delivery to prevent blindness include uveitis, bacterial and fungal endophthalmitis, age-related macular degeneration, viral retinitis, and diabetic retinopathy, among others. For example, the reported incidence of posterior uveitis is more than 100,000 people in the United States. If left untreated, uveitis leads to blindness. It is responsible for about 10 percent of all visual impairment in the U.S. and is the third leading cause of blindness worldwide.

Treatments of intermediate and posterior uveitis are complicated by the inaccessibility of the posterior eye to topically applied medications. Current therapy for intermediate and posterior uveitis requires repeated periocular injections and/or high-dose systemic therapy with corticosteroids. Injections are usually preferred to systemic drug administration because the blood/retinal barrier impedes the passage of most drugs from the systemically circulating blood to the interior of the eye. Therefore large systemic doses are needed to treat intermediate and posterior uveitis, which often result in systemic toxicities including immunosuppression, adrenal suppression, ulcerogenesis, fluid and electrolyte imbalances, fat redistribution and psychological disorders.

Endophthalmitis affects approximately 10,000 people in the United States each year. Endophthalmitis is typically caused by gram-positive bacteria after ocular surgery or trauma, but it can also be fungal or viral in nature. The current method of treating endophthalmitis is direct injection of antimicrobials into the vitreous. Intravitreal injections are necessary because periocular injections and systemic administration do not deliver efficacious amounts of antibiotics to the target sites in the eye. Age-related macular degeneration (AMD) is the leading cause of irreversible loss of central vision in patients over the age of 50. AMD affects more than 15 million people worldwide.

Treatments of posterior eye diseases require intravitreal and periocular injections or systemic drug administration. Systemic administration is usually not preferred because of the resulting systemic toxicity as discussed above. While intravitreal and periocular injections are preferable to systemic administration, the half-life of most injected compounds in the vitreous is relatively short, usually on the scale of just a few hours. Therefore, intravitreal injections require frequent administration. The repeated injections can cause pain, discomfort, intraocular pressure increases, intraocular bleeding, increased chances for infection, and the possibility of retinal detachment. The major complication of periocular injections is accidental perforation of the globe, which causes pain, retinal detachment, ocular hypertension, and intraocular hemorrhage. Other possible complications of periocular injections include pain, central retinal artery/vein occlusion, and intraocular pressure increases. Therefore, these methods of ocular drug delivery into the posterior of the eye have significant limitations and major drawbacks. In addition, injections are very poorly accepted by patients. These methods also involve high healthcare cost due to the involvement of skilled and experienced physicians to perform the injections.

Ocular iontophoresis is a noninvasive technique used to deliver compounds of interest into the interior of a patient's eye. In practice, two iontophoretic electrodes are used in order to complete an electrical circuit. In traditional, transscleral iontophoresis, at least one of the electrodes is considered to be an active iontophoretic electrode, while the other may be considered as a return, inactive, or indifferent electrode. The active electrode is typically placed on an eye surface, and the return electrode is typically placed remote from the eye, for example on the earlobe. The compound of interest is transported at the active electrode across the tissue when a current is applied to the electrodes. Compound transport may occur as a result of a direct electrical field effect (e.g., electrophoresis), an indirect electrical field effect (e.g., electroosmosis), electrically induced pore or transport pathway formation (electroporation), or a combination of any of the foregoing. Examples of currently known iontophoretic devices and methods for ocular drug delivery may be found in U.S. Pat. Nos. 6,319,240; 6,539,251; 6,579,276; 6,697,668, and PCT Publication Nos. WO 03/030989 and WO 03/043689, each of which is incorporated herein by reference.

One potential problem with present ocular iontophoretic methods and devices concerns the actual delivery, or rather, the non-delivery of the drug into the eye tissue. Because the return electrode is located remote from the eye, various conductive pathways may be formed. Such divergence of the electric current will decrease the efficiency of drug delivery to the target sites in the eye, and as a result, much of the drug may be delivered into the tissues surrounding the eye rather than into the eye per se.

Additionally, despite its apparent advantages, iontophoresis is really just a method of limiting the invasiveness of drug delivery into the eye's interior. Once inside the eye, the pharmacokinetics of water soluble compounds are identical to those following intravitreal injections i.e. their half-lives are on the order of a few hours. Therefore, in many cases, traditional iontophoresis must be repeated as frequently as intravitreal injections, leading to patient inconvenience, increased costs, and increased possibility of untoward effects caused by the iontophoretic treatment itself.

The problem of patient compliance may be compounded by the need to receive daily treatment in a medical facility with high healthcare costs and limited resources and practitioners for treating retinal diseases. Existing ocular iontophoresis systems are not patent-friendly, require multiple parts and assembly to practice, and include either clumsy or complicated procedures. As such, they require the involvement of experienced healthcare professionals to perform the treatments. Paraprofessional and/or in-home self administration use of such devices are precluded by the technical complexity of many existing iontophoretic devices, as well as the costs of expensive dose-controlling equipment. Individuals have a greater tendency to deviate from a medication regimen when required to leave home for medical treatment, particularly when such treatment is frequent.

As such, devices, systems, and methods which are capable of minimally invasively, or non-invasively delivering drugs in a convenient, therapeutically effective manner, particularly to the interior of the eye, continue to be sought.

SUMMARY OF THE INVENTION

Accordingly, the present invention provides devices and methods for delivering an active agent into the eye of a subject, with only minimal invasiveness. In one aspect, a device is provided for delivering an active agent into an eye of a subject. Such a device may include an anode assembly having an anode housing and an anode configured to electrically couple to a power source, the anode assembly being configured to contact and remain against a surface of the eye. The device may also include a cathode assembly having a cathode housing and a cathode configured to electrically couple to the power source, the cathode assembly being configured to contact and remain against the surface of the eye. Additionally, the device may include at least one active agent reservoir functionally associated with at least one of the anode assembly and the cathode assembly.

Such an iontophoretic device may also be embodied as a self contained "all-in-one" device. Accordingly, in one aspect a self-contained device for delivering an active agent into the eye of a subject is provided. Such a device may include a device housing, a first electrode assembly located at least partially within the housing and having a first electrode and a reservoir configured to contain the active agent, the first electrode assembly being configured to contact and remain against a surface of the eye for a sufficient amount of time to deliver the active agent to the eye, and a second electrode assembly located at least partially within the housing and having a second electrode configured to be opposite in polarity from the first electrode. The device may further include a power source located at least partially within the housing and electrically coupled to the first electrode and to the second electrode. Such a self-contained device may be configured such that the power source, first and second electrode assemblies, conductive connections that electrically couple the power source to the electrode assemblies, etc., are all located substantially or completely within the housing of the device. In some cases, the device may be configured such that the subject's eyelids may close substantially completely thereover. In one aspect, the device may be configured as a contact lens. In another aspect, the device may be configured as a scleral lens or scleral shell.

Additionally, the present invention provides methods for delivery of an active agent into the eye of a subject. For example, in one aspect a method is provided for controlling delivery of an active agent to a localized area in an eye of a subject. Such a method may include positioning a device according to aspects of the present invention on an eye surface where the device has an inter-electrode distance between the first electrode assembly and the second electrode assembly that controls the depth and extent of penetration of the active agent within the eye, and iontophoretically delivering the active agent in the eye with the first electrode assembly. The active agent delivered into the eye may provide immediate therapeutic effect, sustained therapeutic effect, or both immediate and sustained therapeutic effect.

The particular active agent to be delivered may be a variety of substances depending on the particular treatment to be effected. Such substances may include drugs in various forms, including prodrugs thereof, and sustained release formulations, as required in order to provide convenient and effective minimally invasive, or non-invasive delivery. Exemplary active agents are enumerated further herein.

DETAILED DESCRIPTION OF THE INVENTION

Before the present systems and methods for ocular drug delivery are disclosed and described, it is to be understood that this invention is not limited to the particular process steps and materials disclosed herein, but is extended to equivalents thereof, as would be recognized by those ordinarily skilled in the relevant arts. It should also be understood that terminology employed herein is used for the purpose of describing particular embodiments only and is not intended to be limiting.

It must be noted that, as used in this specification and the appended claims, the singular forms "a," "an," and, "the" include plural referents unless the context clearly dictates otherwise. Thus, for example, reference to "a polymer" includes reference to one or more of such polymers, and "an excipient" includes reference to one or more of such excipients.

DEFINITIONS

In describing and claiming the present invention, the following terminology will be used in accordance with the definitions set forth below.

As used herein, "formulation" and "composition" may be used interchangeably herein, and refer to a combination of two or more elements, or substances. In some embodiments a composition may include an active agent, an excipient, or a carrier to enhance delivery or depot formation.

As used herein, "active agent," "bioactive agent," "pharmaceutically active agent," and "pharmaceutical," may be used interchangeably to refer to an agent or substance that has measurable specified or selected physiologic activity when administered to a subject in a significant or effective amount. It is to be understood that the term "drug" is expressly encompassed by the present definition as many drugs and prodrugs are known to have specific physiologic activities. These terms of art are well-known in the pharmaceutical, and medicinal arts. Examples of drugs useful in the present invention include without limitation, steroids, antibacterials, antivirals, antifungals, antiprotozoals, antimetabolites, immunosuppressive agents, VEGF inhibitors, ICAM inhibitors, antibodies, protein kinase C inhibitors, chemotherapeutic agents, neuroprotective agents, nucleic acid derivatives, aptamers, proteins, enzymes, peptides, and polypeptides.

As used herein "prodrug" refers to a molecule that will convert into a drug (its commonly known pharmacological active form). Prodrugs themselves can also be pharmacologically active, and therefore are also expressly included within the definition of an "active agent" as recited above. For example, dexamethasone phosphate can be classified as a prodrug of dexamethasone, and triamcinolone acetonide phosphate can be classified as a prodrug of triamcinolone acetonide.

As used herein, "effective amount," and "sufficient amount" may be used interchangeably and refer to an amount of an ingredient which, when included in a composition, is sufficient to achieve an intended compositional or physiological effect. Thus, a "therapeutically effective amount" refers to a non-toxic, but sufficient amount of an active agent, to achieve therapeutic results in treating a condition for which the active agent is known to be effective. It is understood that various biological factors may affect the ability of a substance to perform its intended task. Therefore, an "effective amount" or a "therapeutically effective amount" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a subjective decision. The determination of an effective amount is well within the ordinary skill in the art of pharmaceutical sciences and medicine. See, for example, Meiner and Tonascia, "Clinical Trials: Design, Conduct, and Analysis," *Monographs in Epidemiology and Biostatistics*, Vol. 8 (1986), incorporated herein by reference.

As used herein, "sclera" refers to the sclera tissue in the eye or the conjunctiva between the limbus and the fornix on the surface of the eye, which is the white part of the eye. "Sclera" is also used in referring to other eye tissues.

As used herein, "subject" refers to a mammal that may benefit from the administration of a composition or method as recited herein. Examples of subjects include humans, and may also include other animals such as horses, pigs, cattle, dogs, cats, rabbits, and aquatic mammals.

As used herein, "administration," and "administering" refer to the manner in which an active agent, or composition containing such, is presented to a subject. As discussed herein, the present invention is primarily concerned with iontophoretic delivery, especially with ocular delivery.

As used herein, "noninvasive" refers to a form of administration that does not rupture or puncture a biological membrane or structure with a mechanical means across which a drug or compound of interest is being delivered. A number of noninvasive delivery mechanisms are well recognized in the transdermal arts such as patches, and topical formulations. Many of such formulations may employ a chemical penetration enhancer in order to facilitate non-invasive delivery of the active agent. Additionally, other systems or devices that utilize a non-chemical mechanism for enhancing drug penetration, such as iontophoretic devices are also known. "Minimally invasive" refers to a form of administration that punctures a biological membrane or structure but does not cause excessive discomfort to the subjects and severe adverse effects. Examples of "minimally invasive" drug delivery are microneedle, laser, or heat punctuation in transdermal delivery and periocular injections in ocular delivery.

As used herein, "depot" refers to a temporary mass inside a biological tissue or system, which includes a drug that is released from the mass over a period of time. In some aspects, a depot may be formed by the interaction of an active agent with a depot forming agent, such as a complexing ion which will form an active agent complex that is less soluble than the active agent by itself, and thus precipitate in-vivo.

As used herein, the term "body surface" refers to an outer tissue surface of the subject such as tissue surfaces encountered in ocular and transdermal delivery, or mucosal tissues lining a body cavity such as the mouth for buccal delivery or vaginal tract for vaginal delivery. The term "skin" refers to an outer tissue surface of the subject. It is therefore intended that skin also refer to mucosal and epithelial tissues, as well as the outer surfaces of the eye.

As used herein, the terms "electrode assembly," "anode assembly," and "cathode assembly" refer to an assemblies of at least one electrode and a housing at least partially surrounding the electrode. An electrode assembly would thus include an electrode functioning as either an anode or a cathode. Similarly, an anode assembly would include an anode, and a cathode assembly would include a cathode. In some aspects, the housing may be configured to form a reservoir to hold a substance to be delivered to a subject, such as an active agent or a secondary compound. Such a housing may be made of a number of suitable materials. However, in one aspect, such a material may be an electrically non-conductive, or semi-conductive material. In yet another aspect, the electrode assembly may also include a barrier element configured to attach at a distal portion of the housing and therefore rest between the housing and the skin surface or tissue of a subject when the electrode assembly is in use. Such barrier element can be made of an electrically non-conductive material, and in some aspects, such material will be different from the material of the housing. Examples of such materials include without limitation, polymeric materials, such as adhesives or resins, rubbers, etc.

As used herein, the terms "anode" and "cathode" refer to the electrical polarity of an electrode. The terms "anode" and "cathode" are well known in the art. It should be noted, however, that in some aspects these descriptive terms may be transitory. When using alternating current, for example, two electrodes will alternate between anode and cathode as the current alternates in electrical polarity.

As used herein, the terms "reservoir" and "medicament composition containing subcomponent" may be used interchangeably, and refer to a body or a mass that may contain an active agent, a depot forming agent, secondary compound, or other pharmaceutically useful compound or composition. As such, a reservoir may include any structure that may contain a liquid, a gelatin, a semi-solid, a solid or any other form of active agent or secondary compound known to one of ordinary skill in the art. In some cases, an electrode may be considered to be a reservoir.

As used herein, the term "contact lens" refers to a lens sized to fit approximately over the cornea of the eye.

As used herein, the term "scleral lens" refers to a lens sized to cover and extend beyond the cornea across at least a portion of the sclera of the eye.

As used herein, the term "active electrode" refers to an electrode utilized to iontophoretically deliver an active agent.

As used herein, the term "passive electrode" refers to an electrode that is used to complete an electrical circuit without delivering a compound or substance to a subject.

As used herein, the term "return electrode" refers to an electrode utilized to complete an electrical circuit for active electrode. In one aspect, a return electrode may be an active electrode used to deliver a secondary compound, such as an active agent, a depot forming agent, etc. In another aspect, a return electrode may be a passive electrode.

As used herein, the term "self-contained" refers to a device that contains therein, or substantially therein, all the components required for use. For example, a self-contained iontophoretic device may contain active agents, reservoirs, electrodes, power supplies, etc., within a single housing.

As used herein, the term "reacting" refers to any force, change in environmental conditions, presence or encounter of other chemical agent, etc. that alters the active agent. For example, "reacting" between the active agent and the depot forming agent can be physical or chemical interactions.

As used herein, the term "precipitate" refers to anything less than fully solubilized. As such, a precipitate can include not only crystals, but also gels, semi-solids, increased molecular weight, etc.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc.

This same principle applies to ranges reciting only one numerical value. Furthermore, such an interpretation should apply regardless of the breadth of the range or the characteristics being described.

The Invention

The present invention provides devices and methods for delivering an active agent into the eye of a subject. In one aspect, a device is provided for delivering an active agent into an eye of a subject. Such a device may include an anode assembly having an anode housing and an anode configured to electrically couple to a power source, the anode assembly being configured to contact and remain against a surface of the eye. The device may also include a cathode assembly having a cathode housing and a cathode configured to electrically couple to the power source, the cathode assembly being configured to contact and remain against the surface of the eye. Additionally, the device may include at least one active agent reservoir functionally associated with at least one of the anode assembly and the cathode assembly.

Such an iontophoretic device may also be embodied as a self contained device. Accordingly, in one aspect a self-contained device for delivering an active agent into the eye of a subject is provided. Such a device may include a device housing, a first electrode assembly located at least partially within the housing and having a first electrode and a reservoir configured to contain the active agent, the first electrode assembly being configured to contact and remain against a surface of the eye for a sufficient amount of time to deliver the active agent to the eye, and a second electrode assembly located at least partially within the housing and having a second electrode configured to be opposite in polarity from the first electrode. The device may further include a power source located at least partially within the housing and electrically coupled to the first electrode and to the second electrode. Such a self-contained device may be configured such that the power source, first and second electrode assemblies, conductive connections that electrically couple the power source to the electrode assemblies, etc., are all located substantially or completely within the housing of the device. In some cases, the device may be configured such that the subject's eyelids may close substantially completely thereover. In one aspect, the device may be configured as a contact lens. In another aspect, the device may be configured as a scleral lens or scleral shell.

The placement of both an anode assembly and a cathode assembly on the surface of the eye may enhance penetration of the active agent into the eye, as compared to devices which do not place both the anode and cathode assemblies on a surface of the eye, thus facilitating the localization of such agents in ocular tissues for the treatment of various medical conditions. In addition to increased drug delivery due to such novel placement of the anode assembly with respect to the cathode assembly, it has also been discovered that ocular drug therapy may be enhanced through increased patient compliance by providing methods and devices that are easy to use and that may be utilized by an individual at home. This can be accomplished by incorporating all of the physical elements required for iontophoresis into a self-contained device. In some aspects, such devices may be intended for a single use, following which they may be disposed of, similar to many disposable contact and scleral lenses. In addition to simplifying use, disposable devices decrease the risk of infections and other eye-related conditions common to ocular procedures.

Prior methods of ocular delivery of an active agent often locate return electrodes remote from the eye. Such configurations are inconvenient and allow various conductive pathways to be formed across the tissues surrounding the eye rather than focused only in the eye per se. Placing both the anode assembly and the cathode assembly on the surface of the eye may facilitate the passage of electrical current transsclerally into the eye under the anode and cathode, particularly when current movement across the surface of the eye is limited. In one aspect, the anode assembly and the cathode assembly may be respectively configured on the surface of the eye such that the anode and the cathode complete an electrical circuit substantially within the eye of the subject. In other words, the current between the anode and the cathode may pass predominantly through the eye tissues rather than into or through the connective tissues surrounding the eye. In one aspect, both the anode and the cathode may be oriented within the anode and cathode assemblies to face the surface of the eye. The anode and the cathode may directly contact the surface of the eye, or they may contact the surface of the eye through an intermediate material or reservoir that is part of the device. In either case, such a "direct" contact between the electrodes and the eye surface may facilitate the focusing of electrical current within the eye.

The relative spacing or the inter-electrode distance between the anode and the cathode may play an important role in determining where an active agent is localized in the eye upon delivery. As such, in accordance with one aspect of the present invention, the anode and the cathode may be spaced at an inter-electrode distance which controls the depth and extent of penetration of the active agent within the eye. Such a spacing may focus the electric field more effectively within the eye, thus more effectively delivering the active agent. Increasing the inter-electrode distance will generally cause current to flow deeper into the eye, thus iontophoretically delivering the active agent deeper. Small inter-electrode distances will cause a more superficial delivery of active agent into the eye. Thus, by altering the physical locations of each of the electrode assemblies, and thus the inter-electrode distance between them, the active agent can be delivered to particular regions of the eye at specific depths. As such, the inter-electrode distance may vary depending on the intended delivery location. In one aspect of the present invention, however, the inter-electrode distance may be less than about 40.0 mm. In yet another aspect, the inter-electrode distance may be from about 1 mm to about 10 mm. In a further aspect, the inter-electrode distance may be from about 0.3 mm to about 4 mm.

It is intended that an electrode assembly include at least one electrode. In some aspects, an electrode assembly may also include a reservoir configured to contain an active agent or other compound to be delivered. In other aspects, an electrode assembly may also include at least one barrier element. For example, in one aspect an electrode assembly may include an electrode, an electrically insulating barrier element, and a reservoir configured to contain an active agent or secondary compound. In another aspect, an electrode assembly may include an anode or a cathode and a reservoir.

The anode and cathode associated with the respective electrode assemblies are intended to pass current due to a potential difference established therebetween by a power source. The current acts to move an active agent iontophoretically in a direction that is dependent on the charge characteristics of the active agent and the charge orientation of the potential difference between the anode and the cathode. An active electrode, whether it be an anode or a cathode, is designed to deliver electrical current across an associated reservoir to iontophoretically deliver the active agent located therein. In one aspect, one electrode may be an active electrode and the other electrode may be a return electrode for merely completing the electrical circuit. For example, the active electrode may be an anode and the return electrode may be a cathode, or vice versa. In another aspect, one both the anode and the cathode may each have an associated reservoir for the delivery of compounds. The compounds may be the same or different, depending on the intended use and/or configuration of the device. In those aspects where the compounds are different, both compounds may be active agents, or one compound may be an active agent and one compound may be a compound having no known therapeutic effect. One example of a compound that may have no therapeutic effect is a depot forming agent. The anode and the cathode can be of the same or different size relative to each other. Also, the surface area of one or both electrodes can be configured to modify their respective current densities when in use.

The anode and cathode can be of any material or manufacture known to one skilled in the art. Various examples include metal electrodes, conductive glass electrodes, etc. A single electrode may be coupled to a single reservoir or to multiple reservoirs depending on the particular configuration of a given electrode assembly. Conversely, multiple electrodes having the same polarity may be coupled to a single reservoir in certain aspects. Additionally, in some aspects of the present invention, one of the electrodes may also be a reservoir, with a secondary compound being delivered from the body of the electrode.

The devices the present invention may include an electrically insulating barrier located between the anode and the cathode to preclude or reduce electrical current flow across the surface of the eye. By preventing current flow across the eye surface between the anode and the cathode, current is focused, or forced transsclerally into the eye to complete an electrical circuit. In one aspect, the barrier element located on the device between the anode and the cathode and configured to contact the surface of the eye. As such, the barrier element is configured to electrically isolate the anode from the cathode at the surface of the eye. In another aspect, the barrier element may surround each of the anode assembly and the cathode assembly at the surface of the eye to preclude the passage of fluid and minimize current flow between the anode and the cathode. The barrier element may be constructed of any electrically inert material known that is capable of forming a barrier. The barrier element material may be the same material as the reservoir and/or the device housing, or it may be a different material selected for its dielectric properties. The barrier element may also be physically coupled to the electrode assembly, or it may be a protruding portion of a reservoir or a protruding portion of the device housing, and thus be continuous with the housing or reservoir. In those aspects where the barrier element is not continuous with the housing or reservoir, the barrier element may be comprised of a material that is either the same or different from either the device housing or the reservoir material. Non-limiting examples of barrier element materials may include plastics, composites, nylons, polyesters, polyurethanes, polyethylenes, polycarbonates, etc. Barrier element materials may also include conductive materials such as metals provided the material is rendered non-conductive by coating or other means.

In one aspect, the barrier element may be a lip-seal, and it may form a seal substantially around each of the electrode assemblies. The distance of the separation between the electrode assemblies may depend on the dielectric properties of the material disposed therebetween, and thus may be highly variable. In one aspect, the separation may be from about 0.05 mm to about 5 mm. In another aspect, the separation may be from about 0.1 mm to about 3 mm. In yet another aspect, the separation may be from about 0.2 mm to about 1 mm. In a side-by-side electrode assembly configuration, the distance of the separation between the reservoirs can also be used to control the depth of the penetration and the distribution of the agents in the tissue from the body surface.

In one aspect, electrical isolation can be accomplished by applying a temporary sealant between the electrical assemblies and the eye surface. In addition to directing electrical current through the tissue, such a sealant may also advantageously function to temporarily affix and hold the electrode assemblies in place on the body surface. Sealants may be any useful insulative material known to one skilled in the art, for example and without limitation, gels, waxes, adhesives, impermeable polymeric or resinous materials, etc.

The power sources of the present invention may be any component known to one of ordinary skill in the art that is capable of powering an iontophoretic device. Powering the iontophoretic device includes providing an electrical current or an electrical potential facilitating the delivery of an active agent. In those aspects having power sources self-contained within the device housing, it may be beneficial for the power source to be a flexible battery or the like. Conductive subcomponents may be utilized to electrically couple the power source to the anode within the anode assembly and to the cathode within the cathode assembly. These conductive subcomponents may include wires, traces, microelectronics, or other conductive materials such as conductive fluids within insulated tubing or channels. Such microelectronics may be useful in controlling the delivery of the active agent, and/or for safety purposes. Self-contained aspects may particularly benefit from configurations having the conductive subcomponents substantially or completely embedded within the housing material. In this way, the device allows the subject to blink fairly normally, thus reducing the irritation of the administration of the active agent, and thus increasing patient compliance. In another aspect of a self-contained device, any of the power source, electronic circuitry, conductive subcomponents, etc., may be housed completely or partially in a protruding portion of the device housing. Such a protruding portion may include, for example, a handle used to manipulate the device.

The reservoirs according to aspects of the present invention are designed to hold an active agent or other secondary compound to be delivered prior to administration through the eye tissues of a subject. Such reservoirs are configured to receive electrical current from an electrode to thus iontophoretically deliver an active agent or other compound therefrom. In one aspect, a reservoir may be a distinct compartment, having a lumen for holding an active agent or other secondary compound to be delivered. Additionally, such a reservoir may contain at least one access port to allow the reservoir to be filled while in contact with the body surface of the subject. This configuration may allow the reservoir to be filled during use as the agent within is depleted. In another aspect, a reservoir may be filled during manufacture of the device with an active agent or other secondary compound to be delivered, particularly in those aspects where the device is intended for a single use. Various iontophoretic reservoir materials are known to those skilled in the art, and all are considered to be within the scope of the present invention. Additionally, the active agent or secondary compound may be included in the reservoir in any form, including, without limitation, a liquid, gelatinous, semi-solid, or solid form. In another aspect the reservoir may consist of a portion of the active electrode, such that an active agent or secondary compound is delivered from the electrode when electrical current is introduced.

For optimal iontophoretic delivery of active agents and other compounds into the eye, a permselective material may be placed in ion-conducting relation to the eye surface. An electric current of AC, DC, and AC with superimposed DC can be used to transport the compound of interest through the permselective material into the eye. The permselective material is capable of hindering iontophoretic transport of a competing ion and thus may increase the transference efficiency of the active agent or other compound of interest during iontophoresis. As a result, the active agent may be delivered iontophoretically into the eye more efficiently than iontophoresis without the permselective material. For example, more efficient iontophoretic transport can be achieved by placing the permselective material against an active electrode (e.g., Ag/AgCl) between the electrode and a reservoir to prevent the products of electrochemical reactions generated at the electrode surface (e.g., Ag or Cl ions) from moving into the reservoir. Another example is to place the permselective material at the interface between the surface of the eye and the device. As such, the permselective material may be located between the eye surface and the reservoir to prevent the migration of the active agent and endogenous ions into a reservoir containing a secondary compound of opposite charge, or vice versa the secondary compound and endogenous ions into the active agent reservoir during iontophoresis. Any permselective material capable of hindering iontophoretic transport of a competing ion during iontophoretic transport of the compound of interest may be used in conjunction with the invention. The permselective material may be provided in any of a number of forms as described in applicant's copending U.S. patent application Ser. No. 10/371,148 entitled "METHODS AND SYSTEMS FOR CONTROLLING AND/OR INCREASING IONTOPHORETIC FLUX", filed on Feb. 21, 2003, which is incorporated herein by reference. For example, the material may be provided in a liquid, partially liquid, gelled, partially solid, or fully solid state. In some instances, the permselective material may be supported by a support structure such as an additional membrane having sufficient porosity and chemical inertness so as to avoid interfering with the performance of the permselective material, yet having sufficient mechanical integrity for ease in handling. The material can also be provided in the form of a membrane having a surface sized and/or shaped for direct contact with the eye or shaped for direct contact with an active electrode (e.g., Ag/AgCl). In other instances, the permselective material may be comprised of a polyelectrolyte, which can be a single molecule or an aggregate of molecules having ions or ionizable groups. Additionally, in one aspect a permselective material may be functionally coupled to an electrode delivering an active agent or secondary compound, and/or to an electrode merely completing the electrical circuit.

Numerous configurations for the housings of the devices of the present invention are contemplated, for both single-use and multiple-use devices. In one aspect, the housing may be configured to allow the eyelids of the subject to close substantially completely thereover. In other words, when the device is in contact with the eye, the subject may be able to blink in a fairly normal fashion. Such devices may be configured to resemble a contact lens or a scleral lens. It is also contemplated that devices may be utilized that have irregular shapes, thus differing from the common circular and oval shapes of such lenses, such as half-moon or kidney shapes. In another aspect, the housing may be configured to substantially enclose all conductive connections between the power source and both the return electrode assembly and the active electrode assembly. In this manner, the device would allow simple insertion onto the surface of the eye, and would facilitate substantially normal eye closure and blinking during use. This is particular advantageous in ocular iontophoresis that it provides an easy-to-use all-in-one device and improves patient compliance, especially, when multiple applications are required. Additionally, in those aspects where the device is self-contained, the distance between the electrode assemblies and the power source is necessarily limited. For example, in one aspect the active electrode assembly and the power source may be separated by a distance of less than 40.0 mm. In another aspect, the active electrode assembly and the power source may be separated by a distance of less than 20.0 mm. In yet another aspect, the active electrode assembly and the power source may be separated by a distance of less than 10.0 mm.

Various materials are contemplated for use as the housing that may securely hold the various components of the device while providing dielectric properties sufficient to maintain these components in electrical isolation. It may be additionally beneficial to utilize materials that provide some level of flexibility to avoid damage or irritation to the eye surface. Any material having properties beneficial to the construction of such a device would be considered to be within the scope of the present invention. For example, the housing material may include, without limitation, plastics, metals, composites, Teflon, nylons, polyesters, polyurethanes, polyethylenes, polycarbonates, etc. Materials such as metals may be utilized that are conductive, and thus would need have dielectric materials incorporated therein in order to maintain electrical isolation between various components of the device through the housing.

The housing may also have an associated suction mechanism to create depressurization between the device and the surface of the eye to hold the device onto the eye during treatment. Such a suction mechanism may even hold the device in place during blinking. Depressurization may occur in a reservoir of the device or in a separate suction chamber. Following delivery of the active agent, the device can be pressurized at the interface surface to allow release and subsequent removal. Control of the pressurization and depressurization of the device may be incorporated into the device housing, into a manipulation handle, or any other convenient location. Additionally, the depressurization may be accomplished by the shape of the device housing alone. For example, a device housing conforming to the surface of the eye may be depressurized by merely applying pressure to the device. Removal of such a device may, however, be more problematic that a device having a means to control pressurization, such as a valve element.

Various device configurations are contemplated that allow the iontophoretic administration of an active agent through the eye tissue of a subject in order to provide a therapeutic effect. For example, devices may be constructed wherein the electrode assemblies are in a single integrated unit. In one aspect, the anode assembly and the cathode assembly may be configured adjacent one another within the integrated single unit. Alternatively, devices may be constructed as a collection of separate electrode assemblies or arrays that function as a single unit. As such, in one aspect of the present invention, a device may be a single integral unit to contain and deliver the active agent. Such a device may have separate electrode assemblies, one to deliver an active agent and one to act as a return. In another aspect, both electrode assemblies may be used to deliver active agents and/or secondary compounds. Each of these electrode assemblies may be placed in contact with the eye surface though which the active agent or secondary compound is to be iontophoretically administered. Additionally, the shape of the device may be configured to conform to an eye surface. In such a configuration, the electrode assemblies may be in contact with various tissue structures in the eye, such as the conjunctiva, limbus, cornea, etc. In one aspect, a portion of the device may cover the cornea with at least one reservoir or barrier element being in contact with the conjunctiva. The portion covering the cornea may provide a better fit of the device onto the eye. In another aspect, the device may extend into the cul-de-sac under the eyelids for the same purpose. The portion of the device in the cul-de-sac can also hold an electrode assembly, electrode assemblies, or barrier elements in contact with the conjunctiva.

Various placement configurations of electrode assemblies are contemplated. For example, in many cases side-by-side electrode assembly configurations may be beneficial. Such a configuration may allow effective iontophoresis at a target location while minimizing the extent of the movement of the electrical current in other parts of the body. This is particularly beneficial when administering an active agent to sensitive areas such as the eye, where potential adverse effects may be caused by excessive electrical current passing through particularly sensitive tissues such as the retina in the back of the eye, the optic nerve, etc. Numerous placement configurations are possible, and those discussed herein should not be seen as limiting. In one aspect the electrode assemblies can be located side-by-side on the conjunctiva and sclera. In another aspect, one electrode assembly may be located in the inferior cul-de-sac and the other electrode assembly may be located in the superior cul-de-sac. The active agent may be delivered to various tissue regions depending on the relative locations of the electrode assemblies, such as the sclera, conjunctival, subconjuctival space, ciliary body, choroids, retina, anterior chamber, vitreous, etc. The preferred site may depend on the site of drug action in the eye to provide a pharmacological effect.

While administration to nearly any portion of the eye may be suitable, in one aspect, the active agent or secondary compound may be delivered deeply within the eye by spacing the electrode assemblies relatively far apart. When electrical current is applied through the electrodes, the active agent or secondary compound is released and travels in a moving front through the electrical field. By spacing the electrode assemblies relatively far apart the electric field will penetrate deeper into the eye tissue, and as such, the compound will be delivered substantially deeper into the eye. Delivering an active agent to the center of the globe of the eye may be beneficial because such a location is fairly distant from the vascular clearance beds of the retina and choroids, thus improving retention of the active agent. Such a deep delivery may be accomplished by positioning one electrode assembly in the inferior cul-de-sac and the other electrode assembly in the superior cul-de-sac, or vice versa. In another embodiment as an example, when the electrode assemblies are placed on the pars plana next to the limbus, the site of delivery is preferably in the posterior chamber under the electrodes and the anterior chamber. When the electrode assemblies are placed near the fornix, the site of delivery is the conjunctiva and sclera under the electrodes.

Various side-by-side configurations for the electrode assemblies are possible, depending on the desired delivery location of an active agent, the efficacy of a depot formation, the desired depot location, patient comfort, the active agent/depot forming agent configuration, etc. In one aspect, the electrode assemblies may be placed adjacent to each other, and may be of various shapes such as, without limitation, circles, ovals, triangles, squares, rectangles, polygons, trapezoids, etc. Adjacent may include any relative orientation such as superior to inferior, lateral to medial, or any diagonal combination thereof, as is more fully described herein.

Figure 1:
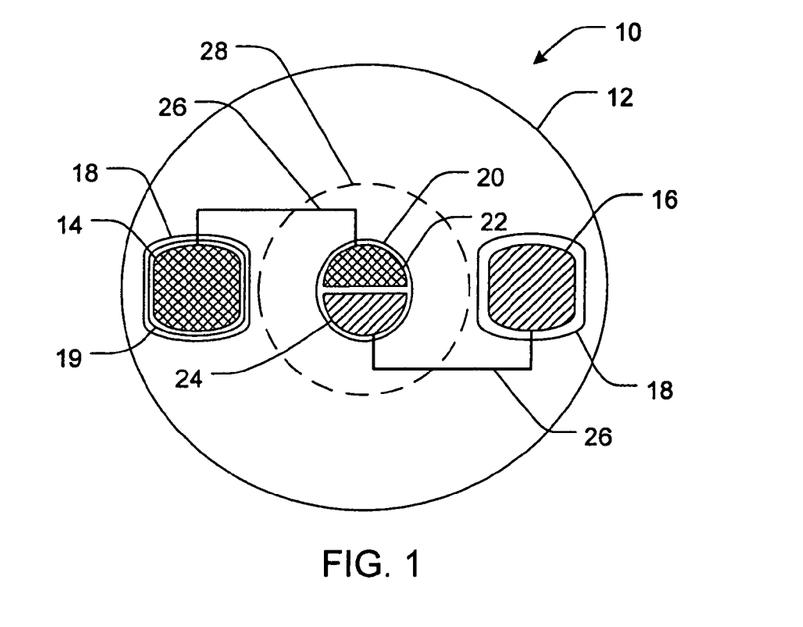
FIG. 1 is a front view of an iontophoretic device in accordance with an aspect of the present invention.

Referring now to FIG. 1, one embodiment of an iontophoretic device in accordance with the present invention is shown. Iontophoretic device 10 is provided having a device housing 12 that is configured to conform the eye of the subject. The device 10 may include an anode assembly 14 and a cathode assembly 16. The electrode assemblies can be spatially arranged in any configuration relative to one another within the device housing 12. Each of these electrode assemblies may be surrounded by a barrier 18 to preclude conduction of current across the surface of the eye and thus focus current into the eye. In one aspect, the electrode assemblies may be present in the device housing without a surrounding barrier (not shown). One or more active agent reservoirs 19 may be associated with at least one of the anode assembly 14 and the cathode assembly 16. FIG. 1 shows the active agent reservoir 19 associated with the anode assembly. A power source 20 is located centrally within the device housing 12. In another aspect the power source may be located in the housing outside of the region 28 located over the eye's limbus, so as not to obstruct the vision of the subject. The power source 20 may include a negative pole 22 electrically coupled to the anode assembly 14 via a conductive trace 26 and a positive pole 24 electrically coupled to the cathode assembly 16 via a conductive trace 26.

Figure 2:
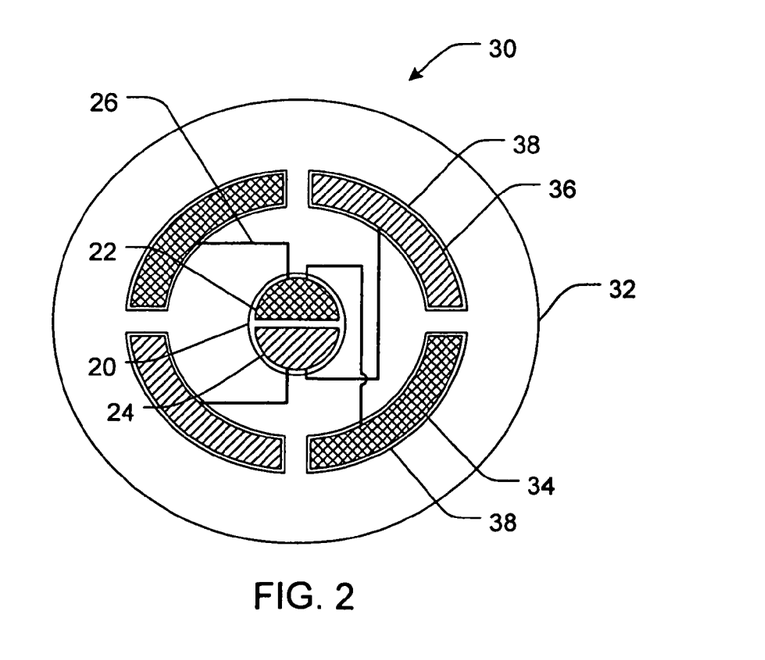
FIG. 2 is a front view of an iontophoretic device in accordance with another aspect of the present invention.

FIG. 2 shows an embodiment of an iontophoretic device 30 having a device housing 32 including two anode assemblies 34 and two cathode assemblies 36. The electrode assemblies may be arranged in an annular arrangement as shown, or in any other arrangement that is beneficial to the delivery of an active agent in a subject. The anode assemblies 34 may each deliver the same active agent or they may deliver different active agents having similar charge, or one or both may merely act as return electrodes. Similarly, both cathode assemblies 36 can each deliver the same or different active agents, or one or both may also merely act as return electrodes. Additionally, any of the electrode assemblies may deliver a secondary compound. Each electrode assembly may be surrounded by a barrier 38 to preclude conduction of electrical current across the surface of the eye. The device 30 additionally includes a power source 20, a negative pole 22, a positive pole 24, conductive traces 26, and reservoirs (not shown) as described in FIG. 1.

Figure 3:
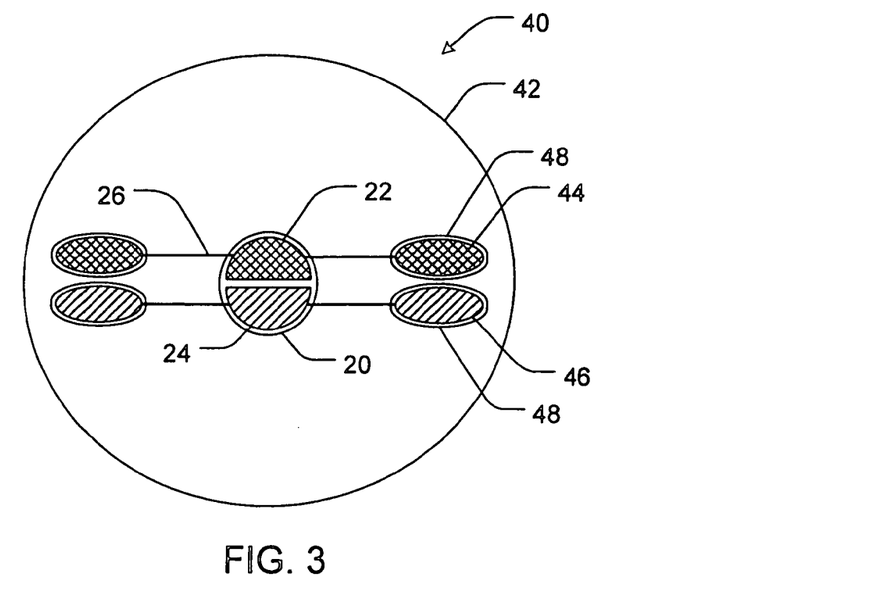
FIG. 3 is a front view of an iontophoretic device in accordance with yet another aspect of the present invention.

FIG. 3 shows yet another embodiment of an iontophoretic device 40 having a device housing 42 including two anode assemblies 44 and two cathode assemblies 46. The electrodes assemblies may be spatially arranged along a single axis as shown, or along multiple axes. The electrode assemblies may be arranged in electrode assembly pairs, with each pair including an anode assembly 44 and a cathode assembly 46. As has been described, the relative locations of the electrode assembly pairs and the relative spacing of the electrode assemblies within the pairs may determine the delivery location(s) of the active agent and any delivered secondary compound. The anode assemblies 44 may each deliver the same active agent or they may deliver different active agents having similar charge, or one or both may merely act as return electrodes. Similarly, both cathode assemblies 46 can each deliver the same or different active agents, or one or both may also merely act as return electrodes. Additionally, any of the electrode assemblies may deliver a secondary compound. Each electrode assembly may be surrounded by a barrier 48 to preclude conduction of electrical current across the surface of the eye. The device 40 additionally includes a power source 20, a negative pole 22, a positive pole 24, conductive traces 26, and reservoirs (not shown) as described in FIG. 1.

Figure 4:
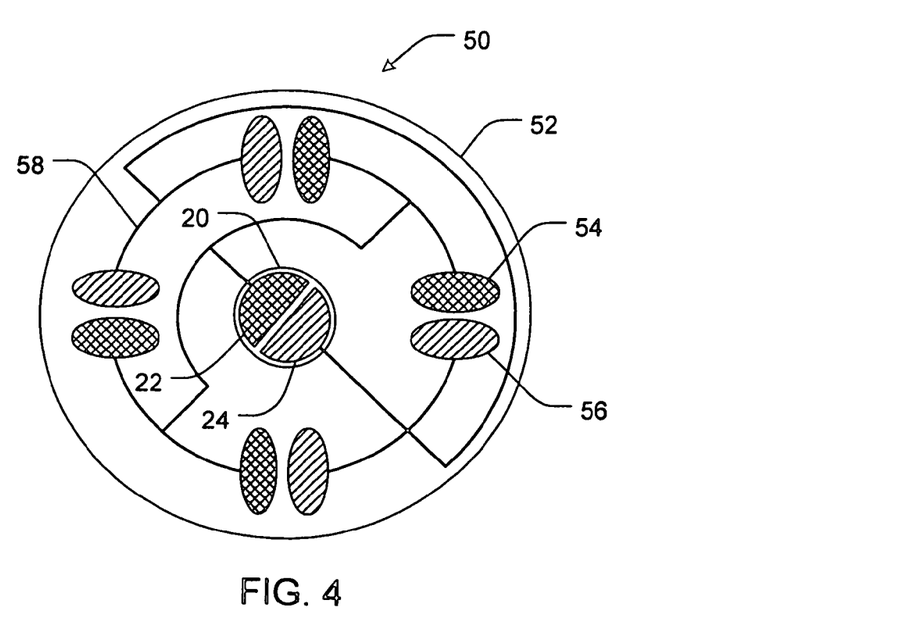
FIG. 4 is a front view of an iontophoretic device in accordance with a further aspect of the present invention.

FIG. 4 shows an additional embodiment of an iontophoretic device 50 having a device housing 52 including four anode assemblies 54 and four cathode assemblies 56 that locally interact to function as four electrode assembly pairs. As such, active agent can be delivered to at least four locations within the eye. As shown, the conductive traces 26 electrically couple each electrode assembly to the power source 20 so as to concurrently deliver active agent to at least four locations within the eye. In an alternative embodiment, conductive traces may be configured such that active agent is delivered to at least four locations consecutively, or in an alternating fashion. As such, the amount of electrical current concurrently delivered to the eye may be limited. As has been described in the previous FIGS., the relative locations of the electrode assembly pairs and the relative spacing of the electrode assemblies within the pairs may determine the delivery location(s) of the active agent and any delivered secondary compound. Also, each electrode assembly may be surrounded by a barrier (not shown) to preclude conduction of electrical current across the surface of the eye. The device 50 additionally includes a power source 20, a negative pole 22, a positive pole 24, conductive traces 26, and reservoirs (not shown) as described in FIG. 1.

Figure 5:
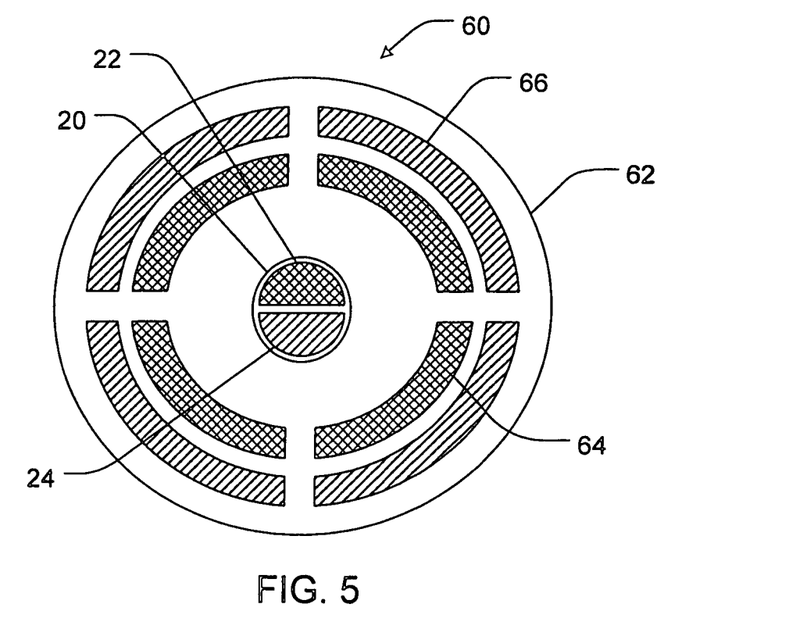
FIG. 5 is a front view of an iontophoretic device in accordance with another aspect of the present invention.

FIG. 5 shows another embodiment of an iontophoretic device 60 having a device housing 62 including four anode assemblies 64 and four cathode assemblies 66. The electrode assemblies may be arranged in an annular arrangement as shown, or in any other arrangement that is beneficial to the delivery of an active agent in a subject. As has been discussed in the previous FIGS., the anode assemblies 64 may each deliver the same active agent, different active agents having similar charge, or act as return electrodes. Similarly, the cathode assemblies 66 can deliver the same or different active agents, or act as return electrodes. Each electrode assembly may be surrounded by a barrier (not shown) to preclude conduction of electrical current across the surface of the eye. The device 60 additionally includes a power source 20, a negative pole 22, a positive pole 24, conductive traces (not shown), and reservoirs (not shown) as described in FIG. 1.

Figure 6:
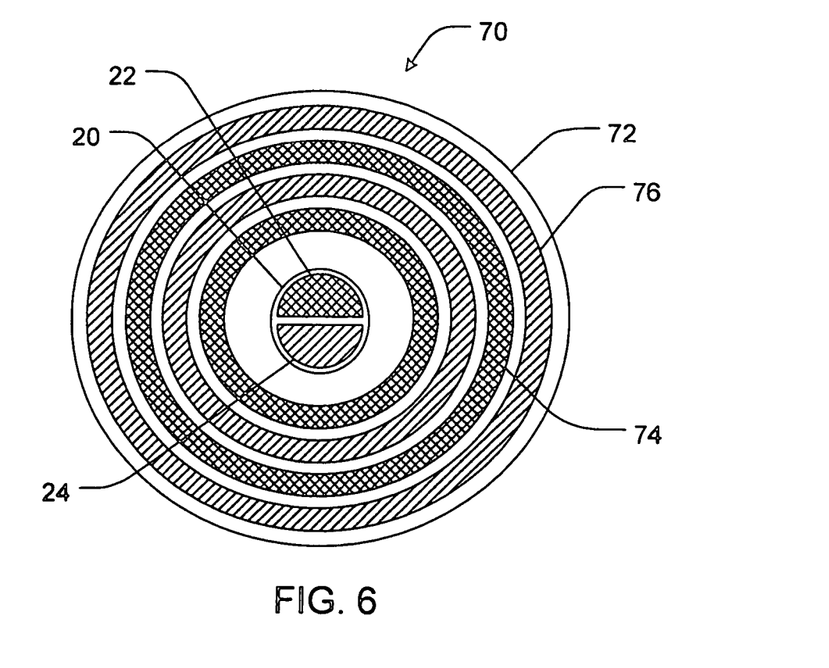
FIG. 6 is a front view of an iontophoretic device in accordance with yet another aspect of the present invention.

FIG. 6 shows yet another embodiment of an iontophoretic device 70 having a device housing 72 including two anode assemblies 74 and two cathode assemblies 76. The electrode assemblies may be arranged in a bullseye pattern as shown, or in any other arrangement that is beneficial to the delivery of an active agent in a subject. As such, each electrode assembly may be a complete or substantially complete circle, having alternating anode and cathode assemblies nested within one another. Electrode assemblies may be activated concurrently to deliver active agent simultaneously, or they may be activated consecutively. The number of electrode assemblies shown in FIG. 6 is merely exemplary, and any number may be included in a particular aspect and still be within the scope of the present invention. As was described in the previous FIGS, each electrode assembly may be surrounded by a barrier (not shown) to preclude conduction of electrical current across the surface of the eye. The device 70 additionally includes a power source 20, a negative pole 22, a positive pole 24, conductive traces (not shown), and reservoirs (not shown) as described in FIG. 1.

Figure 7:
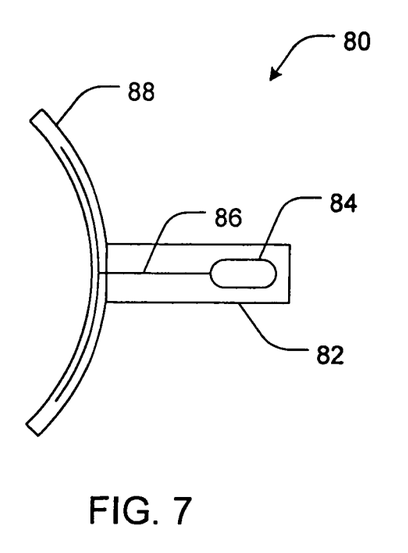
FIG. 7 is a cross sectional view of an iontophoretic device in accordance with a further aspect of the present invention.

FIG. 7 shows one example embodiment of an iontophoretic device 80 having a handle 82 to assist in the manipulation of the device 80. As has been previously described, an iontophoretic device according to various aspects of the present invention may be self-contained, and thus include within the housing all components necessary for the functioning of the device. It should be understood that such a self-contained device may also include aspects having components located within the handle that are not required to be in contact or near the surface of the eye. For example, as shown in FIG. 7, a power source 84 may be located within the handle 82 of the device 80. Conductive traces 86 may electrically couple the power source 84 to the electrode assemblies (not shown) located within the device housing 88. Additional components that may be located within the device housing 88 may include, without limitation, conductive subcomponents, suction manipulation devices, microelectronics, etc.

The present invention also includes methods for controlling delivery of an active agent to a localized area in an eye of a subject. Such a method may include positioning a device according to aspects of the present invention on an eye surface, with the device having an inter-electrode distance between a first electrode assembly and a second electrode assembly that controls the depth and extent of penetration of the active agent within the eye, and iontophoretically delivering the active agent in the eye with at least the first electrode assembly. Such a method may be performed to administer an active agent into the eye to treat various ocular and/or systemic medical conditions.

Though numerous conditions would benefit from the methods and devices of the present invention, they are particularly well suited for the treatment of ocular diseases such as direct, combinatory, and adjunctive therapies. This is because of the relatively high permeability of the eye tissues and the large aqueous compartments in the eye. Examples of eye diseases include without limitation, macular edema, age related macular degeneration, anterior, intermediate, and posterior uveitis, HSV retinitis, diabetic retinopathy, bacterial, fungal, or viral endophthalmitis, eye cancers, glioblastomas, glaucoma, and glaucomatous degradation of the optic nerve.

Accordingly, a wide range of active agents may be used in the present invention as will be recognized by those of ordinary skill in the art. In fact, any agent that may be beneficial to a subject when administered ocularly may be used. Examples of the active agents that may be used in the treatment of various conditions include, without limitation, analeptic agents, analgesic agents, anesthetic agents, antiasthmatic agents, antiarthritic agents, anticancer agents, anticholinergic agents, anticonvulsant agents, antidepressant agents, antidiabetic agents, antidiarrheal agents, antiemetic agents, antihelminthic agents, antihistamines, antihyperlipidemic agents, antihypertensive agents, anti-infective agents, antiinflammatory agents, antimigraine agents, antineoplastic agents, antiparkinsonism drugs, antipruritic agents, antipsychotic agents, antipyretic agents, antispasmodic agents, antitubercular agents, antiulcer agents, antiviral agents, anxiolytic agents, appetite suppressants, attention deficit disorder and attention deficit hyperactivity disorder drugs, cardiovascular agents including calcium channel blockers, antianginal agents, central nervous system ("CNS") agents, beta-blockers and antiarrhythmic agents, central nervous system stimulants, diuretics, genetic materials, hormonolytics, hypnotics, hypoglycemic agents, immunosuppressive agents, muscle relaxants, narcotic antagonists, nicotine, nutritional agents, parasympatholytics, peptide drugs, psychostimulants, sedatives, steroids, smoking cessation agents, sympathomimetics, tranquilizers, vasodilators, β-agonists, and tocolytic agents, and mixtures thereof.

Additionally, further examples of active agents may include steroids, aminosteroids, antibacterials, antivirals, antifungals, antiprotozoals, antimetabolites, VEGF inhibitors, ICAM inhibitors, antibodies, protein kinase C inhibitors, chemotherapeutic agents, immunosuppressive agents, neuroprotective agents, analgesic agents, nucleic acid derivatives, aptamers, proteins, enzymes, peptides, polypeptides and mixtures thereof. Specific examples of useful antiviral active agents include acyclovir or derivatives thereof.

Specific examples of active agents may also include hydromorphone, dexamethasone phosphate, amikacin, oligonucleotides, $F_{ab}$ peptides, PEG-oligonucleotides, salicylate, tropicamide, methotrexate, 5-fluorouracil, squalamine, triamcinolone acetonide, diclofenac, combretastatin A4, mycophenolate mofetil, mycophenolic acid, and mixtures thereof.

Under a number of circumstances, the active agent used may be a prodrug, or in prodrug form. Prodrugs for nearly any desired active agent will be readily recognized by those of ordinary skill in the art. Additionally, prodrugs with high electromobility which metabolize into drugs with a low aqueous solubility may be beneficial. In this case, an electrically mobile prodrug of a low solubility drug in iontophoresis can be used to create a sustained release system in the eye. Because the prodrug has high electromobility, it is effectively delivered into the eye. The prodrug then converts into the low solubility drug in the eye and the insoluble drug precipitates in the eye. The drug in solid state in the eye will be slowly released into the eye and provide an ocular sustained release condition.

Though any prodrug would be considered to be within the scope of the present invention, examples may include the derivatives of steroids, antibacterials, antivirals, antifungals, antiprotozoals, antimetabolites, VEGF inhibitors, ICAM inhibitors, antibodies, protein kinase C inhibitors, chemotherapeutic agents, immunosuppressive agents, neuroprotective agents, analgesic agents, nucleic acid derivatives, aptamers, proteins, enzymes, peptides, polypeptides, and mixtures thereof. One specific example of a steroid derivative may include triamcinolone acetonide phosphate or other derivatives of triamcinolone acetonide, dexamethasone phosphate. For example, it may be preferable to label a steroid with one or more phosphate, sulfate, or carbonate functional groups, so the prodrug can be effectively delivered into the eye and form a complex with the precipitating ion.

In some cases, ocular treatment may be hampered by the in-vivo movement/clearance of the active agent in the eye. It is therefore contemplated that various means for restricting or slowing such movement may improve the effectiveness of the active agent therapy. In one aspect, the in-vivo movement may be restricted by constriction of the blood vessels exiting an area in which the active agent is being delivered or precipitated. Such constriction may be induced by the administration of a vasoconstricting agent. Such a vasoconstrictor may be administered actively by iontophoretic or other means, or it may be delivered passively. Specific non-limiting examples of vasoconstricting agents may include α-agonists such as naphazoline, and tetrahydrozoline, sympathomimetics such as phenylethylamine, epinephrine, norepinephrine, dopamine, dobutamine, colterol, ethylnorepinephrine, isoproterenol, isoetharine, metaproterenol, terbutaline, metearaminol, phenylephrine, tyramine, hydroxyamphetamine, ritrodrine, prenalterol, methoxyamine, albuterol, amphetamine, methamphetamine, benzphetamine, ephedrine, phenylpropanolamine, methentermine, phentermine, fenfluramine, propylhexedrine, diethylpropion, phenmetrazine, and phendimetrazine. Vasocontricting agents can be administered either before or concurrently with the administration of the active agent. Though administration of the vasoconstrictor may occur following administration of the active agent, the results may be less effective than prior or concurrent administration. Additionally, in some aspects, the vasoconstricting agent may have the same polarity as the active agent and administered concurrently with the active agent. Similarly, the vasoconstricting agent may have the opposite polarity as active agent, and thus be administered from a return electrode assembly.

Additionally, in another aspect of the present invention, in-vivo movement may be restricted by constriction of blood vessels as a result of the application of physical force to the blood vessels.

It may also be beneficial for the application situs to be sealed with a sealant following delivery of the active agent.

This procedure may protect the tissue in which iontophoretic administration occurred. Sealants may include any known to one of ordinary skill in the art, including gels, glues and impermeable polymeric or resinous membranes.

Various treatment regimens according to aspects of the present invention are contemplated. In one aspect, the administered active agent may provide an immediate therapeutic effect. In another aspect, the active agent may provide a sustained therapeutic effect. In yet another aspect, the active agent may provide an immediate therapeutic effect and a sustained therapeutic effect. In many cases, some form of sustained release may be beneficial in order to reduce the frequency of administration. Such a reduction in administration may increase patient compliance and reduce the frequency of eye infections and other related issues due to the decreased physical contact with the eye.

Various methods of providing sustained release, and therefore sustained therapeutic effect, are contemplated, some of which have been discussed herein. Such a sustained release may be due to a property of the active agent, the use of a prodrug, the use of a sustained release depot, etc. In one aspect, a sustained release depot may be formed by the reaction of an active agent with a depot forming agent in the eye tissue, following delivery of the active agent to the subject. The depot forming agent may be delivered to the subject, or it may be an endogenous substance that reacts with the active agent. In either case, the depot forming agent and the active agent do not interact with one another until the active agent is delivered into the subject. As such, in most cases the active agent and the depot forming agent will be separated until both are located in-vivo. If the depot forming agent is to be delivered to the subject, then both agents should be delivered separately. Endogenous depot forming agents will, of course, not come into contact with the active agent until administration occurs. Thus an in-vivo reaction between the active agent and the depot forming agent will cause the active agent or a derivative thereof to form a depot. In one aspect such a depot forming mechanism may be a change in the solubility of the active agent or a derivative of the active agent, thus causing precipitation and subsequent depot formation. This depot of active agent complex is then able to deliver a therapeutic compound to the biological system over time. Such sustained delivery can include local or systemic delivery of the active agent to the subject. As such, in one embodiment, a depot forming agent may be created at a desired location in a subject, and the active agent may be systemically administered and may "collect" at the depot forming agent to form a depot as the active agent circulates through the body. In another aspect, the depot forming agent may not react directly with the active agent, but still functions to facilitate the formation of a sustained release depot. In such a case, the depot forming agent may react with an area of a local environment to cause an alteration therein. The active agent would then react with the altered area of the local environment to form a depot as a result of the changes facilitated by the depot forming agent.

As a sustained release mechanism, it will be recognized that the depot formulation of the present invention generally has an in-vivo solubility that is lower than that of the active agent by itself. In this way, as the active agent dissolves out of the depot over time, a sustained therapeutic effect may be obtained. Further, since the active agent in the depot is unable to have a therapeutic effect until released therefrom, the solubility properties of the depot limit potential toxicity or overdose concerns that would normally arise when delivering a sufficient amount of drug to last over a prolonged period. Further details on such depot administration and depot agents can be found in U.S. patent application Ser. Nos. 11/238,144 and 11/238,104, both filed on Sep. 27, 2005, both of which are incorporated herein by reference.

It should be understood that the above-described arrangements are only illustrative of the application of the principles of the present invention. Numerous modifications and alternative arrangements may be devised by those skilled in the art without departing from the spirit and scope of the present invention. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A self-contained device for delivering an active agent into an eye of a subject, comprising:
   a device housing having a shape to conform to the surface of the eye;
   a first electrode assembly located at least partially within the housing and having a first electrode and a reservoir configured to contain the active agent, said first electrode assembly being oriented within the housing to contact and remain against a surface of the eye during use;
   a second electrode assembly located at least partially within the housing and having a second electrode, said second electrode assembly being oriented within the housing to contact and remain against a surface of the eye during use, wherein the first and second electrode assemblies are positioned within the housing to deliver electrical current transsclerally into the eye while limiting electrical current flow across the surface of the eye to thus complete an electrical circuit substantially within the eye; and
   a power source located at least partially within the housing and electrically coupled to the first electrode and to the second electrode, wherein the first electrode and the second electrode are configured to be opposite in polarity to one another during iontophoretic delivery of an active agent into the eye.

2. The device of claim 1, wherein the first electrode assembly and the second electrode assembly are located substantially within the device housing.

3. The device of claim 1, wherein the second electrode assembly includes a reservoir configured to contain a secondary compound.

4. The device of claim 1, further comprising a barrier element associated with the device housing and located between the first electrode assembly and the second electrode assembly, the barrier element being configured to electrically isolate the first electrode from the second electrode at the surface of the eye.

5. The device of claim 4, wherein the barrier element at least substantially surrounds each of the first electrode assembly and the second electrode assembly at the surface of the eye to preclude the passage of fluid and minimize current flow between the first electrode assembly and the second electrode assembly.

6. The device of claim 5, wherein the barrier element is configured to depressurize a space between the surface of the eye and at least a portion of the barrier element in order to maintain a position of the device.

7. The device of claim 4, wherein the barrier element is continuous with the device housing.

8. The device of claim 1, wherein the device housing is configured to depressurize a space between the surface of the eye and at least a portion of the device housing in order to maintain a position of the device.

9. The device of claim 8, wherein the device housing further includes a suction element configured to cause depressurization.

10. The device of claim 1, wherein the device housing is configured to allow eyelids to close substantially completely thereover.

11. The device of claim 10, wherein the device housing is a contact lens.

12. The device of claim 10, wherein the device housing is a scleral lens.

13. The device of claim 1, further comprising a handle configured to assist manipulation of the device.

14. The device of claim 1, wherein the power source is enclosed substantially within the device housing.

15. The device of claim 1, wherein all conductive connections between the power source and both the first electrode and the second electrode are enclosed substantially within the device housing.

16. The device of claim 1, further including microelectronics located within the device housing to control delivery of the active agent.

17. The device of claim 1, wherein the second electrode is a return electrode.

18. A method of controlling delivery of an active agent to a localized area in an eye of a subject, comprising:
    positioning the device of claim 1 on an eye surface, said device having an inter-electrode distance between the first electrode assembly and the second electrode assembly that controls depth and extent of penetration of the active agent within the eye; and
    iontophoretically delivering the active agent in the eye with at least the first electrode assembly.

19. The method of claim 18, wherein the active agent provides an immediate therapeutic effect.

20. The method of claim 18, wherein the active agent provides a sustained therapeutic effect.

21. The method of claim 18, wherein the active agent provides an immediate therapeutic effect and a sustained therapeutic effect.

* * * * *